US009551685B2

(12) United States Patent
Buck et al.

(10) Patent No.: US 9,551,685 B2
(45) Date of Patent: *Jan. 24, 2017

(54) MICROBIALLY-BASED SENSORS FOR ENVIRONMENTAL MONITORING

(71) Applicant: Cambrian Innovation Inc., Boston, MA (US)

(72) Inventors: Justin Buck, Cambridge, MA (US); Matthew Silver, Cambridge, MA (US)

(73) Assignee: CAMBRIAN INNOVATION INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/694,082

(22) Filed: Apr. 23, 2015

(65) Prior Publication Data

US 2015/0300982 A1  Oct. 22, 2015

Related U.S. Application Data

(63) Continuation of application No. 13/514,817, filed as application No. PCT/US2010/059554 on Dec. 8, 2010, now Pat. No. 9,046,478.
(Continued)

(30) Foreign Application Priority Data

Feb. 24, 2010  (WO) ................ PCT/US2010/025224

(51) Int. Cl.
*G01N 27/327* (2006.01)
*G01N 27/416* (2006.01)
(Continued)

(52) U.S. Cl.
CPC ............. *G01N 27/4168* (2013.01); *C12Q 1/02* (2013.01); *G01N 27/327* (2013.01);
(Continued)

(58) Field of Classification Search
CPC .......... G01N 27/327; C12Q 1/02; C12Q 1/025
See application file for complete search history.

(56) References Cited

U.S. PATENT DOCUMENTS 4,090,940 A   5/1978  Switzgable
5,682,288 A   10/1997 Wani
(Continued)

FOREIGN PATENT DOCUMENTS

EP   0242225 A2   10/1987
EP   573226 A1    12/1993
(Continued)

OTHER PUBLICATIONS

Rabaey et al., "Biofuel Cells Select for Microbial Consortia That Self-Mediate Electron Transfer," Applied and Environmental Microbiology, Sep. 2004, p. 5373-5382.*
(Continued)

*Primary Examiner* — Alexander Noguerola
(74) *Attorney, Agent, or Firm* — Wilmer Cutler Pickering Hale and Dorr

(57) ABSTRACT

The present invention relates to the field of surface water monitoring. More specifically, the present invention provides low-cost, real-time bio-electrochemical sensors for surface water monitoring based on the metabolism of one or more electrogenic microbes.

24 Claims, 2 Drawing Sheets

Related U.S. Application Data

(60) Provisional application No. 61/267,594, filed on Dec. 8, 2009.

(51) Int. Cl.
    *C12Q 1/02*     (2006.01)
    *G01N 33/18*     (2006.01)
    *G01N 27/404*     (2006.01)
    *G01N 33/00*     (2006.01)

(52) U.S. Cl.
    CPC ....... *G01N 27/404* (2013.01); *G01N 33/1866* (2013.01); *G01N 33/0037* (2013.01); *G01N 33/0044* (2013.01); *G01N 33/0054* (2013.01); *G01N 33/182* (2013.01)

(56) References Cited

U.S. PATENT DOCUMENTS

| | | | |
|---|---|---|---|
| 6,114,172 | A | 9/2000 | Siepmann |
| 9,046,478 | B2 * | 6/2015 | Buck ................. G01N 33/1866 |
| 2002/0134674 | A1 | 9/2002 | Andrews et al. |
| 2004/0040868 | A1 | 3/2004 | DeNuzzio et al. |
| 2005/0164331 | A1 | 7/2005 | Kim et al. |
| 2005/0183964 | A1 | 8/2005 | Roberts et al. |
| 2006/0037896 | A1 | 2/2006 | Cote et al. |
| 2008/0138663 | A1 | 6/2008 | Kubo et al. |
| 2008/0277273 | A1 | 11/2008 | Logan |
| 2009/0142627 | A1 | 6/2009 | Shimomura et al. |
| 2009/0250394 | A1 | 10/2009 | Taylor |
| 2009/0305084 | A1 | 12/2009 | Crookes et al. |
| 2009/0317882 | A1 | 12/2009 | Cheng et al. |
| 2010/0175821 | A1 | 7/2010 | Cho et al. |
| 2010/0267161 | A1 | 10/2010 | Wu et al. |
| 2010/0270158 | A1 | 10/2010 | Logan |
| 2012/0132521 | A1 | 5/2012 | Silver et al. |
| 2013/0017414 | A1 | 1/2013 | He |

FOREIGN PATENT DOCUMENTS

| | | |
|---|---|---|
| EP | 0667521 A1 | 8/1995 |
| JP | 57-022551 | 2/1982 |
| JP | 05-010921 B2 | 1/1993 |
| JP | H10-230293 A | 9/1998 |
| JP | 11-010184 | 1/1999 |
| JP | H11-216496 A | 8/1999 |
| JP | H11-253993 A | 9/1999 |
| JP | 2000-024687 A | 1/2000 |
| JP | 2000-051894 A | 2/2000 |
| JP | 2000-126794 A | 5/2000 |
| JP | 2000-157995 A | 6/2000 |
| JP | 2001-145896 A | 5/2001 |
| JP | 2002-086189 A | 3/2002 |
| JP | 2002520032 A | 7/2002 |
| JP | 2005-125172 A | 5/2005 |
| JP | 2006-35158 | 2/2006 |
| JP | 2007-117995 A | 5/2007 |
| JP | 2007-227216 A | 9/2007 |
| JP | 2008-114191 A | 5/2008 |
| JP | 2009-222667 A | 10/2009 |
| JP | 2009-258024 A | 11/2009 |
| WO | WO-0003447 A1 | 1/2000 |
| WO | WO-2004004036 A2 | 1/2004 |
| WO | WO-2008059331 A2 | 5/2008 |
| WO | WO-2008103028 A1 | 8/2008 |
| WO | WO-2009072887 A1 | 6/2009 |
| WO | WO-2009131452 A1 | 10/2009 |
| WO | WO-2009155587 A2 | 12/2009 |
| WO | WO-2010044983 A2 | 4/2010 |
| WO | WO-2010147683 A1 | 12/2010 |
| WO | WO-2011000084 A1 | 1/2011 |
| WO | WO-2011003081 A1 | 1/2011 |
| WO | WO-2012011984 A1 | 1/2012 |

OTHER PUBLICATIONS

Arnold, et al., "Regulation of Dissimilatory Fe(III) Reduction Activity in *Shewanella putrefacien,*" *App and Env Microbiol*, vol. 56, No. 9, pp. 2811-2817 (Sep. 1990).
BCC Research, "Environmental Sensing and Monitoring Technologies: Global Markets," a BCC Research Instrumentation & Sensor Report, Oct. 2011 (IAS030B) (5 pgs.).
Beliaev, et al., "Global transciptome analysis of Shewanella oneidensis MR-1 exposed to different terminal electron acceptors," *J Bacteriol*, vol. 187, No. 20, pp. 7138-7145 (Oct. 2005).
Biffinger, et al., "A Biofilm Enhanced Miniature Microbial Fuel Cell Using Shewanella Oneidensis DSP10 and Oxygen Reduction Cathodes," *Biosensors and Bioelectronics*, vol. 22, pp. 1672-1679 (2007).
Bourgeois, et al., "On-Line Monitoring of Wastewater Quality: A Review," *Journal of Chemical Technology & Biotechnology*, vol. 76, pp. 337-348 (2001).
Bretschger, et al., "Current Production and Metal Oxide Reduction by Shewanella oneidensis MR-1 Wild Type and Mutants," *App and Env Microbiol*, vol. 73, No. 21, pp. 7003-7012 (2007), including "Erratum," *App and Env Microbiol*, vol. 74, No. 2, pp. 553 (2008); 12 pages.
Chang, et al., "Improvement of a microbial fuel cell performance as a BOD sensor using respiratory inhibitors," *Biosensors and Bioelectronic*, vol. 20, pp. 1856-1859 (2005).
Chang, I., "Continuous determination of biochemical oxygen demand using microbial fuel cell type biosensor," *Biosensors and Bioelectronics*, vol. 19, pp. 607-613 (2004).
Cheng, et al., "Direct Biological Conversion of Electric Current into Methan by Electromethanogenesis," Environmental Science and Technology, American Chemical Society, vol. 43, No. 10, pp. 3953-3958 (Mar. 26, 2009).
Extended European Search Report issued by the European Patent Office for European Application No. 10836646.9 dated Jun. 10, 2015 (6 pgs.).
Cruz-Garcia, et al., "Respiratory nitrate ammonification by Shewanella oneidensis MR-1," *J Bacteriol*, vol. 189, No. 2, pp. 656-662 (Jan. 2007).
David, et al., "Nitrogen balance in and export from an agricultural watershed," *J Environ Qual.*, vol. 26, pp. 1038-1048 (1997).
Dichristina, T.J., "Effects of Nitrate and Nitrite on Dissimilatory Iron Reduction by *Shewanella putrefaciens,*" J Bacteriol, vol. 174, No. 6, pp. 1891-1896 (1992).
Dilorenzo, et al., "A single-chamber microbial fuel cell as a biosensor for wastewaters," Water Research, vol. 43, pp. 3145-3154 (2009).
Dinnes, et al., "Nitrogen Management Strategies to Reduce Nitrate Leaching in Tile-Drained Midwestern Soils," *Agronomy Journal*, vol. 94, pp. 153-171 (2002).
Du, et al., "A State of the Art Review on Microbial Fuel Cells: A Promising Technology for Watewater Treatment and Bioenergy," Biotechnology Advances, vol. 25, pp. 464-482 (2007).
European Supplemental Search Report issued by the European Patent Office for European Patent Application No. EP12800665.7 dated Mar. 10, 2015 (6 pages).
Extended European Search Report issued by the European Patent Office for European Application No. 10789884.3 dated May 16, 2013 (10 pgs.).
Faeth, P., "Fertile Ground: Nutrient Trading's Potential to Cost-Effectively Improve Water Quality," Washington, DC: World Resources Institute, 59 pgs. (2000).
Gieling, et al., "ISE and Chemfet sensors in greenhouse cultivation," *Sensors and Actuators B*, vol. 105, pp. 74-80 (2005).
Gorby, et al., "Electrically conductive bacterial nanowires produced by Shewanella oneidensis strain MR-1 and other microorganisms." *Proceedings of the National Academy of Sciences*, vol. 103, No. 30, pp. 11358-11363 (2006).
Grommen, et al., "Removal of Nitrate in Aquaria by Means of Electrochemically Generated Hydrogen Gas as Electron Donor for Biological Denitrification," *Aquacultural Engineering*, vol. 34, No. 1, pp. 33-39 (2006).

(56) References Cited

OTHER PUBLICATIONS

Holmes, "Potential Role of a Novel Psychrotolerant Member of the Family Geobacteraceae, *Geopsychrobacter electrodiphilus* gen. nov., sp. nov., in Electricity Production by a Marine Sediment Fuel Cell," *Applied and Environmental Microbiology*, vol. 35, pp. 128-133 (2004).

International Search Report and Written Opinion issued by the Korean Intellectual Property Office as International Searching Authority for International Application No. PCT/US2010/025224 mailed Oct. 12, 2010 (10 pgs.).

International Search Report and Written Opinion issued by the Korean Intellectual Property Office as International Searching Authority for International Application No. PCT/US2010/059554 mailed Sep. 26, 2011 (8 pgs.).

International Search Report and Written Opinion issued by the U.S. Patent and Trademark Office as International Searching Authority for International Application No. PCT/US2012/042501 mailed Sep. 28, 2012 (10 pgs.).

Jia, et al., "Simultaneous Organics Removal and Bio-Electrochemical Denitrification in Microbial Fuel Cells," *Bioprocess and Biosystems Engineering*, vol. 31, No. 4, pp. 315-321 (2008).

Joo, et al., "A Microbial Fuel Cell Type Lactate Biosensor Using a Meal-Reducing Baterium, Shewnalla Putrefaciens," J. Microbiol. Biotechnol., vol. 9, No. 3, pp. 365-367 (1999).

Kang, et al.,"A microbial fuel cell with improved cathode reaction as a low biochemical oxygen demand sensor," *Biotechnology Letters*, vol. 25, pp. 1357-1361 (2003).

Kim, et al., "A Microbial Fuel Cell Type Lactate Biosensor Using a Metal-Reducing Bacterium, Shewanella Putrefaciens," J. Microbiol. Biotechnol., vol. 9, No. 3, pp. 365-367 (1999).

Kim, et al., "Membrane-electrode assembly enhances performance of a microbial fuel cell type biological oxygen demand sensor," *Environmental Technology*, vol. 30, No. 4, pp. 329-336 (Apr. 1, 2009).

Kim, et al., "Microbial Fuel Cell-type Biochemical Oxygen Demand Sensor," Encyclopedia of Sensors, pp. 1-12 (2005).

Kim, et al., "Novel BOD (biological oxygen demand) sensor using mediator-less microbial fuel cell," *Biotechnology Letters*, vol. 25, pp. 541-545 (2003).

Kostka, J.E. and Nealson, K.H., "Dissolution and reduction of magnetite by bacteria," *Environmental Science and Technology*, vol. 29, pp. 2535-2540 (1995).

Kumlanghan, et al., "Microbial fuel cell-based biosensor for fast analysis of biodegradable organic matter," *Biosensors and Bioelectronics*, vol. 22, pp. 2939-2944 (2007).

Kuroda, et al., "CO2 Reduction to Methan and Acetate Using a Bio-electro Reactor with Immobilized Methanogens and Homoacetogens on Electrodes," Energy Conversion and Management, vol. 36, No. 6-9, pp. 787-790.

Liu, et al., "Immobilised Activated Sludge Based Biosensor for Biochemical Oxygen Demand Measurement," *Biosensors and Bioelectronics*, vol. 14, No. 12, pp. 883-893 (2000).

Liu, J. and Mattiasson, B., "Microbial BOD Sensors for Wastewater Analysis," *Water Research*, vol. 36, No. 15, pp. 3786-3802 (2002).

Logan, Bruce E, and Regan, John M., "Microbial Fuel Cells: Challenges and Applications." *Environmental Science & Technology*, vol. 40, No. 17, pp. 5172-5180 (Sep. 1, 2006).

Rabaey, et al., "Microbial Fuel Cells: Novel Biotechnology for Energy Generation," Trends in Biotechnology, vol. 23, No. 6, pp. 292-298 (2005).

Ratako, et al., "Micro- and Mini-Nitrate Sensors for Monitoring of Soils, Groundwater and Aquatic Systems," *Center for Embedded Network Sensing*, May 12, 2009, 3 pgs. (2009).

Rezaei, et al., "Substrate-enhanced microbial fuel cells for improved remote power generation and sediment-based systems," *Environ Sci Technol*, vol. 41, pp. 4053-4058 (2007).

Ringeisen, et al., "High Power Density from a Miniature Microbial Fuel Cell Using Shewanella oneidensis DSP10," *Environ. Sci. Technol*, vol. 40, pp. 2629-2634 (2006).

Shantaraman, et al., "Wireless sensors powered by microbial fuel cells," *Environ Sci Technol*, vol. 39, pp. 5037-5042 (2005).

Prasad, et al., "A Microbial Sensor Based on Direct Electron Transfer at *Shwanella* Sp. Drop-Coated Screen-Printed Carbon Electrodes," Electroanalysis, vol. 21, pp. 1646-1650 (Jun. 9, 2009).

Sukkassem, et al., "Effect of Nitrate on the Performance of Single Chamber Air Cathode Microbial Fuel Cells," *Water Research*, vol. 42, pp. 4743-4750 (2008).

Tabacova, et al., "Exposure to Oxidized Nitrogen: Lipid Peroxidation and Neonatal Health Risk," *Archives of Environmental Health: An International Journal*, vol. 53, No. 3 (1998), 9 pages.

Tabacova, et al., "Maternal Exposure to Exogenous Nitrogen Compounds and Complications of Pregnancy," *Archives of Environmental Health: An International Journal*, vol. 52, No. 5, (1997), 8 pages.

Vitousek, et al., "Human Alteration of the Global Nitrogen Cycle: Sources and Consequences," *Ecological Applications*, vol. 7, No. 3 (1997), 15 pages.

Zhang, Yifeng, and Angelidaki, Irini, "Submersible microbial fuel cell sensor for monitoring microbial activity and BOD in groundwater: Focusing on impact of anodic biofilm on sensor applicability," *Biotechnology and Bioengineering*, vol. 108, No. 10, pp. 2339-2347 (2011).

\* cited by examiner

MICROBIALLY-BASED SENSORS FOR ENVIRONMENTAL MONITORING

CROSS-REFERENCE TO RELATED APPLICATIONS

This is a continuation application of U.S. application Ser. No. 13/514,817 filed Dec. 6, 2012, which is the national stage application of International Application No. PCT/US2010/059554, filed Dec. 8, 2010, which claims priority to U.S. Provisional Patent Application No. 61/267,594, filed Dec. 8, 2009 and International Application No. PCT/US2010/025224, filed Feb. 24, 2010. The contents of each of these applications are hereby incorporated by reference in their entireties.

FIELD OF THE INVENTION

The present invention relates to the field of environmental monitoring, and in particular to the development bio-electrochemical sensors for monitoring chemical compound levels in surface water.

BACKGROUND OF THE INVENTION

Surface water nitrate ($NO_3^-$) pollution from agricultural production and other sources is a well-established problem in the United States. For example, nitrate levels in the Mississippi River have more than doubled since 1965 and have increased 3 to 10-fold in the northeastern U.S. since 1990 (Vitousek et al, 1997). The widespread nitrate contamination of waterways across the country has led to significant environmental and human health challenges. In particular, the discovery of large anoxic dead zones in the Gulf of Mexico and the drop of fish populations in the Chesapeake Bay have placed the role of nutrient run-off from our agricultural industry in the public eye. Indeed, contamination in the Gulf of Mexico can be at least partially attributed to agricultural run-off in the Mississippi River Basin and, especially Midwest agricultural areas (USGS, DO1, 2000). It has been found that nitrate loss from agricultural land managed by subsurface or tile drainage systems is particularly high (Dinner, et al., 2002). The common use of these systems in the Midwest states correlates to elevated nitrate runoff. By EPA estimates, nitrate concentrations of up to 40 mg/L exist in and exit tile drainage systems into surface water (Sawyer, et al., 2006). It was also estimated in a 1997 east-central Illinois study that 49% of the inorganic nitrogen pool in agricultural soils was leached to tile drains and 30 exported to streams (David et al., 1997).

Development of efficient and economical tools and methods to mitigate agricultural and other nitrate runoff is therefore imperative. Besides the concerns of regulators, farmers themselves have an interest in managing nitrate concentrations in soils and surface water, as increasing numbers move towards sustainable agriculture and precision application of nutrients for resource efficiency and economic benefit. As the U.S. and other industrialized countries attempt to move towards sustainable economies and deal with existing environmental challenges, there is increasing focus on monitoring nutrients, particularly nitrates, in surface water produced at non-point sources such as agricultural operations and water treatment plants, as well across watersheds more generally.

There are two main technologies currently being used for nitrate sensing, including spectrophotometric devices (UV) and ion-selective electrodes (ISE). These technologies can be utilized in ecological and industrial environments with success. However, there are a number of disadvantages which are halting their widespread utilization, such as generally high cost and short lifetime or labor intensive maintenance, with some specific issues regarding sensing range and precision.

UV sensors are the industry standard for continuous monitoring. They operate by scanning for dissolved nitrate molecules using a 210 nm wavelength light and have a 95% confidence interval for a thirty second scan of 0.2 uM (Johnson and Coletti, 2002). Thus, these systems are typically used for deployments which require high sensing precision with minimal maintenance schedules. They have been used for long-term monitoring in drinking water, freshwater, watershed, marine, and wastewater applications where they are deployed for their high sensitivity (Hach, 2009). There are a variety of UV sensor systems available, along with customized packages, such as sondes, in which they can be installed, but the common characteristic among all of them is that they are capital-intensive devices: ranging from $5,000 (est.) to $15,000 (Hach NITRAX sensors). This cost is due to their complicated design and features (self-calibration, auto-cleaning, pressure-resistant casings, spectrophotometer equipment) which makes them difficult and expensive to fix if broken.

ISE sensors cost less than the UV sensors; at less than $500 (NexSense WQSensors' Nitrate ISE sensor, Hach ISE sensor). However, they have several drawbacks which make them less applicable in critical environments. Their main limitation is sensitivity to temperature and a severe interference by ionic compounds. This leads to one of the most limiting factors for widespread use: their poor performance in marine environments. Since ISEs need to be calibrated often and readings quickly become a function of other ionic compounds' concentrations, temperature, and age of electrode tip, they are typically used in controlled environments such as laboratories or as sensors for site visits (NexSense, 2010) rather than for long-term deployments. Additionally, the electrode tip ($75-$150) needs to be replaced twice a year, quickly adding to over 30% of the initial capital used for upkeep within the first year.

As described, existing methods for monitoring nitrate levels in surface water through periodic field monitoring and sample are labor and materials intensive, expensive (between $500 to $15,000 dollars per sensor, depending on the technology) and short-lived (average time to replace ~6 month, depending on the technology). Moreover, given the mobility of nitrogen, the current monitoring practices give an incomplete picture of ongoing nitrate loss. As such, there is a need for improved, low-cost sensors for surface water monitoring.

SUMMARY OF THE INVENTION

The present invention provides novel, low-cost, real-time bio-electrochemical sensors for environmental monitoring, particularly surface water monitoring. The sensors of the invention are based on the metabolism of one or more types of electricigenic/electrogenic microorganisms and provide an inexpensive, durable, and accurate tool useful to monitoring agencies, research institutions, watershed management organizations, and farmers concerned with monitoring and controlling nutrient run-off over large coverage areas.

In contrast to bio-electrochemical sensors previously described in the art in which the electrical current generated increases in the presence of the target compound for sensing, the sensors of the invention utilize one or more electrogenic microbes which selectively interact with a working electrode in the sensor to produce an electrical current in the absence of the target compound to be detected. In other words, there is an inverse relationship between the electrical current produced and the concentration of the target compound present. As the concentration of the target compound increases, the electrical current produced by the bio-electrochemical sensor decreases. Preferably, a biofilm comprising a plurality of electrogenic microbes is used in the sensor.

The working electrode in the sensors of the invention can be either an anode or a cathode. Where the working electrode is an anode, the sensors of the invention further comprise a controlled chemical cathode, and said target compound is selectively reduced in the sensor. Examples of target compounds that can be detected in such a configuration include electron acceptors such as oxygen, nitrite ($NO_2^-$), nitrate ($NO_3^-$), fumarate, dimethyl sulfoxide, Arsenate ($AsO_4^{-3}$) (e.g., oxidized arsenic), uranium (VI), Molybdenum (VI), Vanadium (V or IV), Vanadate, selenate, selenite, Sulfate ($SO_4^-$), elemental sulfur ($S^0$), chromium (VI), phosphate, phosphite, and/or iron (III). In a particular embodiment, the target compound for detection by the sensors of the invention is nitrate.

Where the working electrode is a cathode, the sensor further comprises a controlled chemical anode, and said target compound is selectively oxidized in the sensor. Examples of target compounds that can be detected in such a configuration include electron donors such as hydrogen ($H_2$), methane ($CH_4$), ammonium ($NH_4^+$), ammonia ($NH_3$), sulfide, iron (H), arsenite, elemental sulfur ($S^0$), chromium (III), uranium (III), molybdenum (V), Vanadium (IV or III), vanadate, reduced phosphate a carbohydrate, and glucose.

The electrogenic microbe utilized in the sensors of the invention can vary, depending on the desired target compound(s) to be monitored. In some embodiments, known or genetically engineered electrogenic microbes incapable of using one or more of the following compounds can be used in the sensors of the invention: oxygen, nitrite ($NO_2^-$), nitrate ($NO_3^-$), fumarate, dimethyl sulfoxide, Arsenate ($AsO_4^{-3}$), uranium (VI), Molybdenum (VI), Vanadium (V or IV), Vanadate, selenate, selenite, Sulfate ($SO_4^-$), elemental sulfur ($S^0$), chromium (VI), phosphate, phosphite, iron (III), hydrogen ($H_2$), methane ($CH_4$), ammonium (($NH_4^+$), ammonia ($NH_3$), sulfide, iron (II), arsenite, chromium (III), uranium (III), molybdenum (V), Vanadium (IV or III), vanadate, reduced phosphate a carbohydrate, or glucose. Examples of suitable microbial strains include *Shewanella, Psuedemonas, Geobacter, Cyanobacteria*, or any known or genetically engineered mutant thereof.

In a particular embodiment, an electrogenic microbe having an inability to utilize nitrite ($NO_2^-$) and/or nitrate ($NO_3^-$) is used in a sensor according to the invention. An example of an electrogenic microbe that is unable to utilize ($NO_2^-$) and/or nitrate ($NO_3^-$) includes, but is not limited to *Shewanella oneidensis* napA⁻.

In a particular embodiment, at least two electrogenic microbes are utilized in a sensor according to the invention. Preferably, the two electrogenic microbes each have a different respiratory phenotype. For example, without limitation, a mutant strain of an electrogenic microbe having an altered respiratory phenotype, and the corresponding wildtype strain of the electrogenic microbe can be used together in the sensor of the invention. A non-limiting example of such mutant and wildtype strains includes, without limitation, wildtype *Shewanella oneidensis* and a mutant *Shewanella oneidensis* such as *Shewanella oneidensis* napA⁻.

The bio-electrochemical sensors of the invention may include a region for sensing/detecting a first target compound, a separate region for sensing/detecting a second target compound, a sample region, and/or a media recirculation system. Preferably, the sample region and the first and second sensor regions are separated by a selectively permeable barrier, such as a filter or a porous membrane. The first and/or second target compounds for detection are preferably in either a gaseous or an aqueous phase. Each of the sensing regions include a unique anode chamber and a unique cathode chamber.

In a particular embodiment, the bio-electrochemical sensor of the invention is designed for detecting/monitoring nitrate. In another particular embodiment, the bio-electrochemical sensor of the invention is designed for detecting/monitoring nitrate and oxygen.

Other features and advantages of the invention will be apparent from the following detailed description and claims.

DETAILED DESCRIPTION

Figure 1:
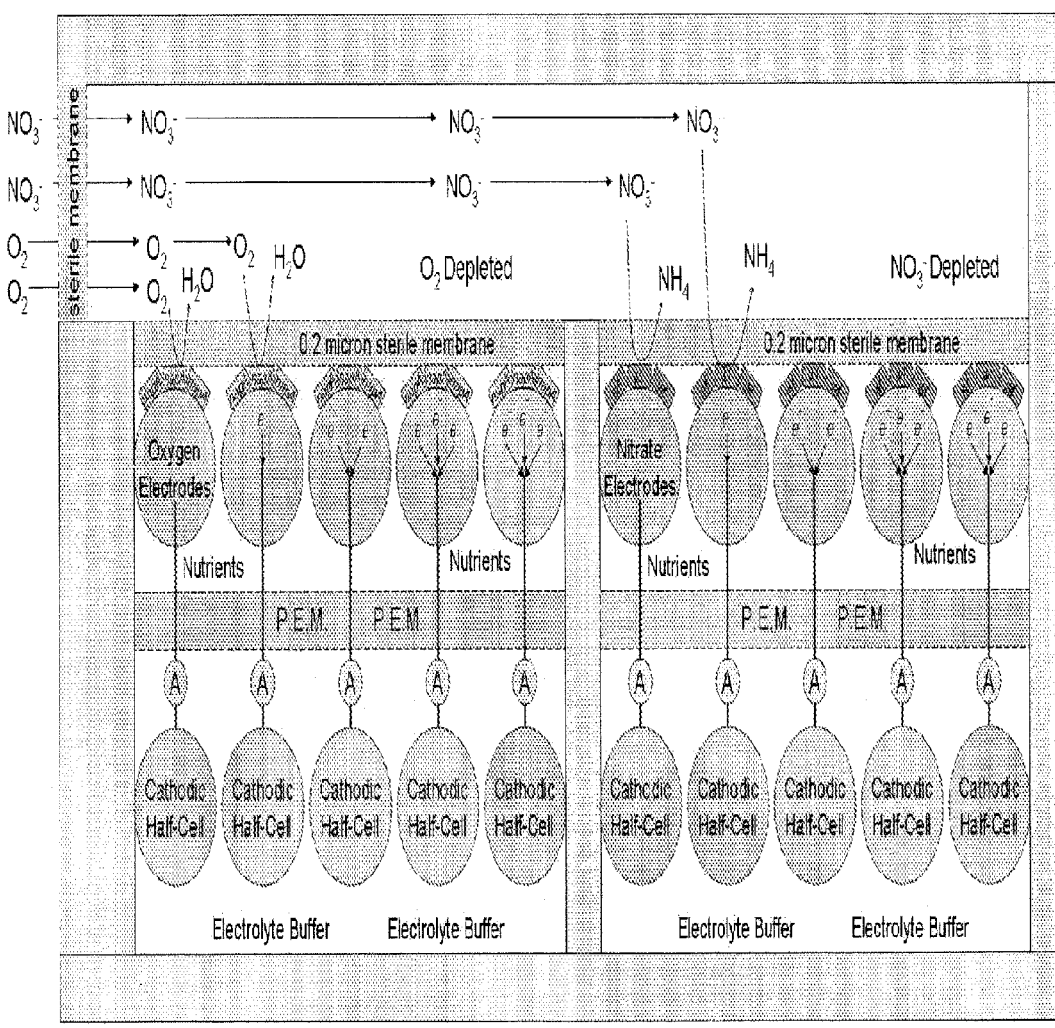
FIG. 1 is a schematic illustrating the design of a microbially-based sensor according to the invention.

Referring now to the drawings, to the following detailed description, and to incorporated materials; detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Microbial Fuel Cells as Sensors

Microbial fuel cells (MFCs) take advantage of bacteria that normally use insoluble metal deposits as electron sinks during anaerobic consumption of reduced substrates. By substituting an electrode for the metal deposits, current can be collected, induced to flow through external circuitry and do electrical work before ultimately arriving in the cathode chamber where electrons reduce a terminal electron acceptor, often oxygen. MFCs generally fall under the category of proton exchange membrane fuel cells (PEMFCs) because a membrane divides the anode and cathode half reactions and allows only selective passage of cations to balance the charge carried by electrons arriving at the cathode through the circuitry. The driving force for electron flow or current is derived from the electrochemical redox difference between the oxidation reaction in the anodic half-cell and the reduction reaction of the terminal electron acceptor at the cathode.

Surprisingly, these electricigenic microbes (sometimes referred to in the art as electrogenic microbes) seem to be ubiquitous in nature, as sediments in many locations provide the microbes to generate electrical currents (Holmes et al, 2004). Microbes utilize several mechanisms to release electrons to the anode: (i) through dissolved exogenous mediator or electron shuttle compounds; (ii) by interspecies electron transfer involving membrane complexes; and, (iii) electron transfer involving conductive pili or nanowires (Gorby et al, 2006). Once transferred to the anode, the electrons flow to the cathode where they participate in the reduction of the terminal electron acceptor. In the case where molecular oxygen is used as the terminal electron acceptor, reduction at the cathode generates water, using protons that have transferred from the anodic chamber across a proton-exchange membrane (PEM).

A number of variations in MFC architecture have been developed resulting in a dramatic $10^5\times$ increase in power production between the earliest versions in 1999 (approx. 0.01 mW/m$^2$ [normalized to anode surface area]) to the most recent architecture reported in 2006 (approx. 1000 mW/m$^2$) (Logan and Reagan, 2006).

Microbial fuel cell performance varies according to a number of physical and chemical parameters of the device, including substrate concentration, temperature and redox state. While perturbations to voltage or amperage output may be deleterious in some applications, this quality also allows MFCs to function as biological sensors for parameters that affect their performance. Anode or cathode substrate concentration is probably the most convenient sensor input.

Indeed, MFCs have been utilized in a number of studies to report on concentration of biological oxygen demand (BOD) or lactate. In one of the earliest examples, a two-chamber MFC containing a potassium ferrocyanide electron acceptor in the cathode was dosed with lactate in the anode containing *Shewanella* sp. bacteria; the rate of increase of current production was correlated to lactate dosage (Kim et al., 1999). A more generalized sensor utilized an air-cathode MFC colonized by *Shewanella* sp. bacteria was used as a sensor for BOD concentration in starch processing plant wastewater by correlated total Coulombs generated in batch mode performance to the starting BOD of the wastewater (Kim et al., 2003). Notably, this sensor used an MFC device that had been established for over 4 years, and showed reproducibility of +/− 13% in sensing BOD concentrations over the course of almost 1 year, demonstrating that MFC-based sensors have a long usable lifetime (Kim et al., 2003).

A more sophisticated version of this BOD sensor was constructed that used a continuous flow MFC for real-time monitoring of BOD by using current output as a proxy (Chang et al., 2004). Two additional studies focus on optimizing the cathodic reaction and MFC architecture to improve sensitivity of the BOD sensor by producing more current per BOD equivalent, and also improved reproducibility drastically, to +/−3% (Kang et al., 2003; Kim et al., 2009). In a similar design, a sensor utilizing a microbial consortium in the anode and a phosphate buffer/salt catholyte solution was shown to produce an increasing voltage with the linear range claimed to be 25 mg/L to 25 g/L glucose (Kumlanghan et al., 2007).

Microbially-Based Sensors of the Invention

In contrast to the MFC-based BOD sensors previously studied which sense the availability of an electron donor in solution, the sensor of the present invention is capable of targeting the availability of electron acceptors in a liquid or gaseous solution. The basic concept behind the sensor is the preferential and hierarchical use of terminal electron acceptors or electron donors in solution (aqueous or gaseous) by microorganisms at either the anode or cathode region, depending on the configuration of the sensor.

Where the sensor is configured such that the working electrode is an anode, the sensors of the invention further comprise a controlled chemical cathode, and said target compound is selectively reduced in the sensor. Examples of target compounds that can be detected in such a configuration include electron acceptors such as oxygen, nitrite ($NO_2^-$), nitrate ($NO_3^-$), fumarate, dimethyl sulfoxide, Arsenate ($AsO_4^{-3}$), uranium (VI), Molybdenum (VI), Vanadium (V or IV), Vanadate, selenate, selenite, Sulfate ($SO_4^-$), elemental sulfur ($S^0$), chromium (VI), phosphate, phosphite, and/or iron (III).

Where the working electrode is a cathode, the sensor further comprises a controlled chemical anode, and said target compound is selectively oxidized in the sensor. Examples of target compounds that can be detected in such a configuration include electron donors such as hydrogen ($H_2$), methane ($CH_4$), ammonium ($NH_4^+$), ammonia ($NH_3$), sulfide (e.g., $H_2S$, HS, and $S^{2-}$), iron (II), arsenite, elemental sulfur ($S^0$), chromium (III), uranium (III), molybdenum (V), Vanadium (IV or III), vanadate, reduced phosphate a carbohydrate, and glucose.

Many microbes have the ability to respire with numerous electron acceptors, including but not limited to, oxygen, nitrite ($NO_2^-$), nitrate ($NO_3^-$), fumarate, dimethyl sulfoxide, Arsenate ($AsO_4^{-3}$), and uranium. In the presence of multiple electron acceptors, microbes typically regulate respiratory pathways to utilize the most energetically favorable electron acceptors first. This hierarchical use of electron acceptors often has several levels. For example, *E. coli*, a well-studied model organism, respires to oxygen even in the presence of all other suitable electron acceptors. If oxygen is depleted and nitrate is present, nitrate will be used before other electron acceptors. Finally, if both oxygen and nitrate are absent *E. coli* will respire to other electron acceptors or ferment in the absence of suitable electron acceptors.

However *E. coli* is not an optimal organism for use in a bio-electrochemical cell-based sensor due to a limited ability to utilize an electrode for respiration and inclination for fermentation. *Shewanella oneidensis* (*S. oneidensis*), on the other hand, has been shown to be effective for conductive anodic biofilm formation (Biffinger et al, 2007) and extracellular transfer at 500 W/m$^3$ (Ringseisen et al 2006). High power density is an important feature as sensing performance will depend on attenuation of the electrical output of the cell. *S. oneidensis* is capable of utilizing a wide range of terminal electron acceptors (Bretschger et al, 2007; Kim et al, 1999; DiChristina 1992; Arnold, et al 1990) and incapable of fermentation (Kostka and Nealson, 1995). *S. oneidensis* has also been shown to produce a differential response in electron acceptor utilization (Belleav et al, 2005). These factors make *S. oneidensis* a model organism for bioelectrochemical cell-based sensing of electron acceptors.

In certain embodiments, the sensors of the invention utilize one or more electrogenic microbes having an altered respiratory phenotype. The altered phenotype can be an altered electron acceptor utilization capacity, or an altered electron donor utilization capacity, depending on the configuration of the sensor, as previously described. For example, the electrogenic microbe can be a known wildtype or mutant microbe, or a genetically engineered microbe that is incapable utilizing electron acceptors such as oxygen, nitrite ($NO_2^-$), nitrate ($NO_3^-$), fumarate, dimethyl sulfoxide, Arsenate ($AsO_4^{-3}$), uranium (VI), Molybdenum (VI), Vanadium (V or IV), Vanadate, selenate, selenite, Sulfate ($SO_4^-$), elemental sulfur ($S^0$), chromium (VI), phosphate, phosphite, and/or iron (III). As a further example, the electrogenic microbe can be a known wildtype or mutant microbe, or a genetically engineered microbe that is incapable of utilizing electron donors such as hydrogen ($H_2$), methane ($CH_4$), ammonium ($NH_4^+$), ammonia ($NH_3$), sulfide (e.g., $H_2S$, HS, and $S^{2-}$), iron (II), arsenite, elemental sulfur ($S^0$), chromium (III), uranium (III), molybdenum (V), Vanadium (IV or III), vanadate, reduced phosphate a carbohydrate, and/or glucose.

Suitable electrogenic microbes that can be used in the sensors of the invention include strains of *Shewanella, Psuedemonas, Geobacter*, and *Cyanobacteria*, including known or genetically engineered mutants thereof.

One embodiment of a microbially-based sensor of the invention is depicted in FIG. 1. The sensor shown in FIG. 1 is designed to detect the amount of oxygen and nitrate present in a sample by determining the distance over which they are capable of diffusing in a controlled chamber before being consumed in respiration. It should be noted that the sensors of the invention are not limited to detecting nitrate and/or oxygen. The sensor depicted in FIG. 1 and described in Example 1 below is merely one example of a sensor designed in accordance with the invention.

As shown in FIG. 1, the sensor is divided into two distinct regions on the interior; the first is the oxygen sensor, and the second is the nitrate sensor. Each region shares a common diffusion chamber, but contains unique anode and cathode chambers. Diffusion of oxygen and nitrate through the sensor is shown from left to right. In the first chamber of the sensor, oxygen is consumed until completion resulting in different levels of current produced on the oxygen bioelectrodes. The nitrate is unaltered in the first chamber because the mutant strain is incapable of using it as a terminal electron acceptor. When the nitrate reaches the second chamber, it is consumed until completion resulting in different levels of current produced on the nitrate bioelectrodes.

The diffusion chamber is maintained sterile by excluding microbes from the external sample and bioanode chambers using a barrier with pore size of less than 0.2 microns, which simultaneously prevents cross-contamination of the sensor and sample. Importantly, this sensor design is an instantiation of a platform design that can be extended to additional electron acceptors. Through the incorporation of additional mutant strains, species, and chambers, a wide range of electron acceptors can be measured. While the first targets are oxygen and nitrate, in the future the sensor could be modified to address water contaminant such as arsenic and uranium for different applications.

Genetically engineered microbes having altered respiratory phenotypes have been described. For example, *S. oneidensis* carrying the mutation napA⁻ has been shown to be incapable of respiring or assimilating nitrate and/or nitrite (Cruz-Garcia 2007). Other microbes can be genetically engineered to carry mutations which render them incapable of utilizing oxygen, arsenic, chromium, sulfate, fumarate, phosphate, and/or iron, and can be used in the sensors of the invention. Likewise, microbes having altered electron donor utilization capacity can be genetically engineered for use in the sensors of the invention.

One or more electricigenic/electrogenic microbes can be used in sensors of the invention. The microbes utilized in the sensors of the invention can vary, depending on the desired target chemical/compound to be monitored. In a preferred embodiment, at least two microbes having different respiratory phenotypes are used in sensors of the invention. By way of example, where the target chemical desired to be monitored is nitrate, *S. oneidensis* carrying the mutation napA⁻ can be used in the oxygen anode, which renders it incapable of respiring or assimilating nitrate and/or nitrite (Cruz-Garcia 2007), and a wild type strain of *S. oneidensis* can be used in the nitrate anode, which renders it capable of using both oxygen and nitrate and/or nitrite. As the sample passes the exterior of the sensor (as shown on the left of FIG. 1), oxygen and nitrate diffuse into the sensor. The microbes at the beginning of the oxygen anode experience concentrations of oxygen and nitrate near levels outside the sensor. These microbes will readily make use of the oxygen as a preferred electron acceptor. In the presence of oxygen, *S. oneidensis* decreases the amount of electron transfer to an external electrode, producing a measurable signal of oxygen presence.

As the oxygen is consumed by microbes at the beginning of the oxygen anode, the amount of oxygen diffusing down the chamber decreases and subsequent microbes experience a reduced oxygen concentration. Progressing further into the sensor, oxygen becomes depleted and the microbes are dependent on respiration to the electrode to maintain metabolic activity. The nitrate level is unaltered by the oxygen anode because the napA⁻ strain is incapable of using nitrate and/or nitrite.

At the entrance to the nitrate region of the sensor, all oxygen has been consumed and nitrate has been unaltered (only a diffusion gradient has been established). At the nitrate anode, the same phenomena present for the oxygen anode will occur; nitrate will be consumed by microbes near the sensor entrance, reducing electrode respiration and consuming nitrate. As nitrate is consumed, electrical current will increase as the microbes once again require extra-cellular electron transfer to sustain metabolic activity. Because the anode wires are arranged perpendicular to the diffusion concentration gradient, each wire and associated microbes experiences a uniform profile of electron acceptors. By interpreting the different electrical currents produced at each of the anode wires, we will determine the presence of the electron acceptors at various locations in the sensor and infer the concentration of the species in the sample based on the concentration profile established.

Sensor Performance

The concentration of electron acceptors within the diffusion chamber can be modeled using principles of transport phenomenon and reaction kinetics. The generalized form of the mass transfer equation is:

$$\frac{\partial C}{\partial t} = D\left[\frac{\partial^2 C}{\partial x^2} + \frac{\partial^2 C}{\partial y^2} + \frac{\partial^2 C}{\partial z^2}\right] - R \quad (1)$$

Where C is the concentration of chemical species (oxygen or nitrate), D is the diffusivity of the chemical species in water, R is the rate of reaction (consumption) of the chemical species, t is time, and x, y, and z are the Cartesian dimensions. This equation specifically accounts for dynamic changes within the system boundaries, diffusion gradients in all three coordinates, and chemical reactions. For our system, this equation can be simplified. First, the gradient term for the z-direction can be eliminated because the concentration is uniform across the entire width of the sensor and only varies across the height and length. Next, it can be assumed that the sensor operates in a quasi-steady state. This reduces the equation to the form:

$$0 = D\left[\frac{\partial^2 C}{\partial x^2} + \frac{\partial^2 C}{\partial y^2}\right] - R \quad (2)$$

From this point, the analysis can take several paths depending on the assumptions made. As the sensor is designed, no reaction occurs in the diffusion chamber and the problem becomes a two-dimensional diffusion problem with fixed boundary conditions at the semi-permeable sterile barriers. While this description is the most accurate for the system, deriving an analytical solution is not trivial and applying boundary conditions becomes quite complicated. For a first approximation of how the sensor will behave, it can be assumed that the height is much smaller than the length of the sensor, thus diffusion in the y-direction is fast compared to x-direction, making the problem one dimensional and much simpler to solve analytically. Rearranging the simplified equation gives the form:

$$R = D \frac{\partial^2 C}{\partial x^2} \quad (3)$$

At this point, it must be determined what form the reaction term takes. The reaction is not occurring in the bulk but rather at the surface (or more precisely on the opposing side of the surface). However, because the problem has been simplified to one dimension, it is a reasonable approximation to indicate a bulk reaction term. Without intending to be bound by theory, the consumption of the electron acceptor will likely have a dependence on the concentration of the electron acceptor. This is caused not only because of the microbial physiology, but also due to the diffusion barrier which must be crossed to reach the anode chamber. A simple approximation for the concentration dependence is linear (one interpretation of which would be complete depletion at the anode and a diffusion limitation to reaction). Using this form gives the following equation:

$$k_R C = D \frac{\partial^2 C}{\partial x^2} \quad (4)$$

This equation is a second order linear homogeneous differential equation with a general solution of the form:

$$C = k_1 e^{x\sqrt{k_R/D}} + k_2 e^{-x\sqrt{k_R/D}} \quad (5)$$

Applying the boundary conditions of C approaching 0 as x approaches infinity and $C=C_0$ at x=0, gives the following solution to the differential equation:

$$C = C_0 e^{-x\sqrt{k_R/D}} \quad (6)$$

This solution indicates that the concentration falls exponentially along the length of the sensor and never reaches zero in theory (although it does in practicality). This equation gives a fair representation of how the concentration profile behaves, but lacking the parameter for the reaction rate constant it is worth considering a simpler model which has a zero-order (constant) reaction rate. In this case, the R in Equation (3) is a constant and the equation can be solved by separation of variables to the general form:

$$C = \frac{R}{2D}x^2 + k_1 x + k_2 \quad (7)$$

When the boundary conditions of C=0 at x=L and total flux at x=0 equals the total reaction rate in the sensor are applied, the following equation is derived:

$$C = \frac{R}{2D}(x - L)^2 \quad (8)$$

Where L is the distance into the chamber at which oxygen is depleted. This equation can be rearranged to solve for the distance into the sensor at which the electron acceptor will be depleted in teens of $C_0$, the concentration at the diffusion chamber entrance (x=0):

$$L = \sqrt{\frac{2DC_0}{R}} \quad (8)$$

Using values for the saturation of oxygen in water at room temperature ($C_0$=9.1 g/m$^3$), diffusivity of oxygen in water at room temperature (D=1.8×10$^{-9}$ m$^2$/s), and an observed rate of bulk oxygen uptake by *S. oneidensis* (R=0.015 g/m$^3$-s Tang et al, 2007), the approximate length at which oxygen will become depleted in the oxygen sensor can be estimated. The result of this calculation is 1.5 mm. While this number indicates a relatively small length, it should be noted that it is on a reasonable scale (millimeters as opposed to micrometers or meters) and that the assumptions for reaction rate are rather conservative, using an exponentially growing cell suspension. In reality, the length over which the electron acceptor is depleted can be fine tuned by altering several of the geometric parameters of the sensor, the most prominent being the height of the diffusion chamber. As the height of the diffusion chamber increases, the volume of liquid (and thus the total amount of electron acceptor) increases while the surface area for the consumption reaction (and thus the rate of reaction) remains constant. Alternatively, by altering the anode chamber volume and the surface area of the electrodes it is possible to modify the electron acceptor consumption rate that will affect the length over which the diffusion gradient is established. For simplicity, these factors have not been analyzed here, but will be addressed by future modeling efforts.

Electrical Considerations of the Sensor Design

The present invention provides microbial fuel cell-based environmental sensors that also fulfills the power requirements needed to remotely transmit gathered data. Several aspects of the sensor design make it amenable to such a system. First, by using chitin as a sacrificial anode substrate with good longevity, the MFC will function and produce power over a period of time likely measured in months or years. As previously shown, when using a very small amount of Chitin-80, a substrate-enhanced MFC was successfully operated for a period of 10 days with no loss in power output, and longevity could be improved at least linearly with the amount of chitin utilized (Rezaei et al., 2007). The sensor of the invention operates so that relatively constant power is produced in the absence of an increased oxygen or nitrate stimulus, and is designed so that concentrations of these interfering chemicals will produce only an incomplete reduction in power output that is still sufficient to generate a transfer of information remotely from the sensor. In the event of an extreme and sustained oxygen or nitrate plume sufficient to completely ablate power production, such a situation would very likely warrant operator intervention to remediate the offending pollutants.

As with other MFC-powered sensors, capacitors must be used to store the steady trickle of charge for a burst of signaling activity, but this technology is well developed and practical considerations have been previously addressed (Shantaram et al., 2005). The magnitude of the sensor response will be correlated to increased current magnitude in one or several of the anode electrode circuits. There are several potential methods available to sense current variations within a wire including Hall effect sensors that produce a charge when current is passed through a permanent magnet, or using a simple operational amplifier-based circuit, currents from 0-200 nA can be reliably sensed by a device costing under $10 to build (Linear Technology, 2010). The configuration of electrical components and current meters may vary, depending on cost, performance and robustness of the components.

Other Sensor Design Considerations

Cathode half-cell design-to avoid limitation and fluctuation in the signal as a result of the cathode, a chemical half-cell with excess capacity and stability over the sensor life is implemented.

Response to temperature—biology and all electrochemistry applications are sensitive to changes in temperature. This parameter is evaluated and possibly controlled in any final sensor design.

Ensuring nutrient availability—for sensor reliability, nutrients must not limit the activity of the microbes. Essential nutrients are provided for the microbes in a long-lasting (slow release) form.

Circuit design for signal analysis—signal derived from the individual anode wires for each sensor are accumulated and processed to determine the concentration of oxygen and nitrate.

Microbe genetic drift—being essential to sensor performance, stability of the microbial community is preserved by preventing cross-contamination using impermeable barriers and seeding the anode with a genetically stable strain.

Biomass accumulation in the sensor—cellular debris may accumulate in the sensor and biofilms may form on barriers between chambers. Microbial fuel cells can sustain long-term stable performance (Kim et al., 2003), but careful design is needed to prevent fouling.

Interference from water constituents—The effects of various water constituents is evaluated at later stages of development for potential toxicity and possibility for signal interference.

INDUSTRIAL APPLICABILITY

Emerging trends in the agricultural, research, wastewater and regulatory fields indicate a significant need for low-cost real-time sensors. For example, EPA documentation, such as its 2006-2011 Strategic Plan already refers to 'Strategic Targets' for nitrate reduction (Johnson, 2006). Initiatives such as the United States Environmental Protection Agency's (EPA) Mississippi River Gulf of Mexico Watershed Nutrient Taskforce, are indicative of an increasing focus on monitoring nitrates in surface water, particularly in connection with agricultural operations. Currently, there are around 41 watersheds involved in the Mississippi River Basin Initiative conducted by the NRCS (annual program funding of $80 million). Soil and water conservation districts and others work with individual producers to monitor nitrate and other nutrients at 'edge of field' in 'next to field' waterways with a view to reducing those levels through improved farm practices (NRCS, 2010). In addition, regions of the country, such as the Midwest, are known for extensive use of tile drainage systems.

Thus, with increased interest in the monitoring and regulation of nitrates in surface water there is a market-driven need for inexpensive, durable, and accurate tools for surface water monitoring in the U.S. In Europe, where nitrates have been regulated since 1991, there is also a market need for high quality, continuous monitoring equipment for the existing network of 27,000 surface water stations established by regulators across Europe (Europa Commission, 2010). In addition, fixed output level on all types of agricultural activity, codes of best practice farming, polluter pays and prevention at source principles, compulsory measures for entities in 'nitrate vulnerable zones' place responsibility for this issue at the individual user level. This has also led to a European market for nitrate sensing equipment at the individual producer level (Gieling et al., 2005). Although a similar regulation has not yet been applied in the US, the European market provides a point of reference should the US move in that direction.

The microbially-based sensors of the present invention are particularly useful for monitoring agricultural run-off, with an emphasis on regions with high usage subsurface tile drainage systems. Given the low cost, durability and sensitivity of the sensor design, the sensors of the invention are useful tools for government agencies, including regulators such as the EPA and the U.S. Department of Agriculture (USDA), agricultural consultants, and individual agricultural holders alike.

Likewise, the microbially-based sensors of the present invention are particularly useful for watershed monitoring and management. Watershed monitoring and data collection appears to be growing as part of the core mission of watershed management associations across the USA. District, city and/or state sponsored watershed management associations are now conducting monitoring activities of local streams, rivers, ponds, reservoirs, and lakes. Such associations typically monitor monthly and rely on volunteers and external lab analysis. The low cost, durability and sensitivity of the sensor design make the sensors of the present invention an ideal tool for use by such watershed management associations.

In addition, an increasing number of water researchers and research centers are focused on water quality, drainage systems, precision farming, transport of nutrients and contaminants, amongst others. The low cost, durability and sensitivity of the microbially-based sensors of the invention make them an ideal tool for use by researchers to monitor nitrates in tile drains, irrigation ditches, streams and rivers etc.

The microbially-based sensors of the invention can also be applied in the field of wastewater treatment.

EXAMPLES

The invention now being generally described, it will be more readily understood by reference to the following example which is included merely for purposes of illustration of certain aspects and embodiments of the present invention, and are not intended to limit the invention in any way.

Example 1

Development of a Microbially-Based Nitrate Sensor

The present example demonstrates the feasibility of using the preferential electron acceptor utilization of *Shewanella oneidensis* as the basis for a microbial sensor. Specifically, the present example aims to:

1) Demonstrate differential current down a concentration gradient of oxygen established by diffusion and respiratory consumption
2) Demonstrate differential current down a concentration gradient of nitrate established by diffusion and respiratory consumption
3) Establish preliminary sensor design based on the parameters of sensor dimensions, consumption rate of electron acceptor, and diffusivity of the electron acceptor species.

The sensor is developed in four parallel steps according to the method outlined below.

Step 1: Construct the Test Cells

Figure 2:
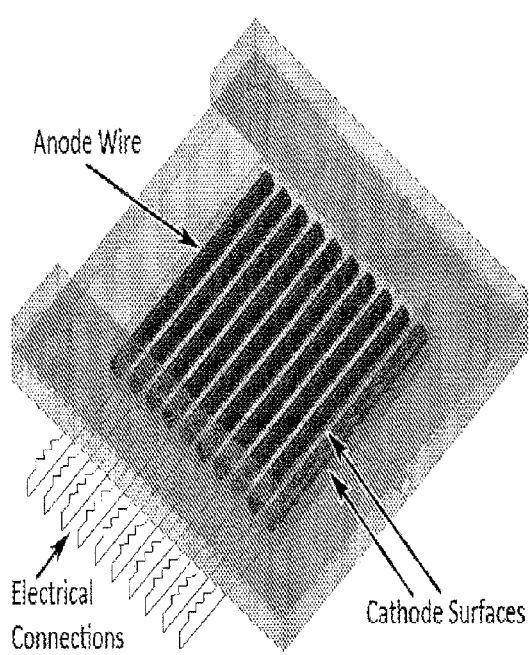
FIG. 2 is a schematic illustrating the sensor region of a microbially-based sensor according to the invention.

The test cells for Phase I is composed of two components, the sensor region and the media recirculation system (FIG. 2). The general design of these components is the same for testing the oxygen and nitrate sensors. Three test cells are fabricated: the oxygen sensor test cell, the nitrate sensor test cell, and the no-acceptor control cell.

The Sensor Region

The sensor region (FIG. 2) is composed of a sample chamber, a diffusion chamber, an anode chamber, and a cathode chamber separated by ion exchange membranes or sterile filters. The structure for each of these chambers is made from a biocompatible polymer material with limited oxygen diffusivity. The sterile filters separating the diffusion chamber from the sample chamber and the anode chamber are made out of a filter of pore size 0.2 um (Pall Supor filter) to ensure no microbial contamination from the anode chamber into the diffusion chamber, sample chamber, and media reservoir. All membranes and plastic pieces are sealed in the sensor assembly using rubber gaskets to prevent leakage and air introduction. All parts for the sensor region are sterilized prior to each experiment.

The sample chamber contains inlet and outlet ports to allow for the constant exchange of fresh media, replenishing both the nutrient supply and the level of the electron acceptor being studied (oxygen or nitrate). Flow through the sample chamber is tangential to the filter, which minimizes any convective flow in the anode chamber while maintaining constant sample concentrations for the establishment of the diffusion gradient.

The anode chamber design has a large length to height aspect ratio to ensure depletion of the electron acceptor and to increase the sensor sensitivity. Anode wires are aligned parallel to the width dimension and extend across the entire chamber to ensure a unique but uniform environment at each wire. The sensitivity and statistical certainty and accuracy directly correlates to the number of wires but increases sensor complexity in cost; this issue is addressed during construction. The anode wires are adjacent to the filter separating the diffusion chamber from the anode chamber. This allows the microbes colonizing the wires to experience the oxygen concentration directly across the filter in the diffusion chamber without consumption and interference from microbes living in the bulk.

The cathode directly opposes the anode and is equally separated from each anode wire. Each anode wire corresponds to a directly opposing cathode lead. This uniform geometry, along with excess cathode capacity, ensures that only the composition of the media will cause variance in anode wire performance. The ion exchange membrane separating the anode chamber from the cathode is made of Nation to minimize oxygen permeation into the anode chamber and minimize MFC internal resistance. The membrane is incorporated directly with the cathode in a membrane electrode assembly composed of a platinum catalyst. The cathode is operated as a standard air cathode. If oxygen leakage into sensor is suspected as a problem, the platinum catalyzed air cathode is replaced with an anaerobic cathode half-cell.

The Media Re-Circulation System

Maintaining a constant concentration of electron acceptor and nutrients is essential to testing the sensor design. This is achieved using a large reservoir of media and re-circulating the media through the sample chamber at a high rate. The size of the reservoir is sufficient to maintain a nearly uniform composition over the duration of the experiment, which can be confirmed by testing for the presence of electron acceptors and nutrients. If necessary, the media in the reservoir can be changed without drastically affecting the sensor component. The reservoir itself may be a large media bottle with a cap modified to contain tubing fittings.

Figure 3:
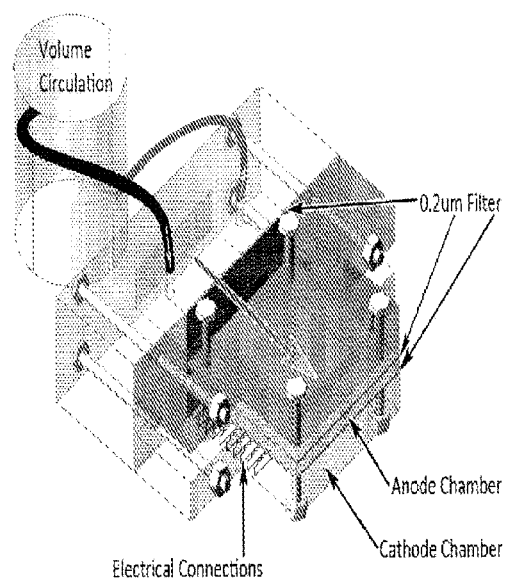
FIG. 3 is a schematic illustrating the media recirculation system of a microbially-based sensor according to the invention.

The reservoir is connected to the sensor with flexible tubing (FIG. 3). A peristaltic pump drives flow from the reservoir into the sample chamber. A separate tube returns the liquid from the sample chamber to the reservoir. The reservoir is well mixed to avoid hydraulic short circuiting and maintain a uniform composition.

Step 2: Verify Oxygen Sensor Principle

Step 2 is divided into three subtasks. The first subtask is to confirm the differential response of the culture in electrode utilization with and without oxygen. Once this is confirmed, the second subtask is to utilize the culture in the sensor test cell to check for the establishment of an oxygen gradient and differential response down that gradient. Finally, varying levels of dissolved oxygen in the media are tested in the third subtask to verify the sensor operation. These subtasks are described in more detail below.

Confirm Differential Response to Oxygen

A culture of *Shewanella oneidensis* MR-1 is inoculated in a conventional MFC. This MFC is conditioned to establish an active anaerobic microbial community engaging in extracellular electron transport. Fresh nutrients are added (anaerobically) in batches to the reactor to maintain constant activity. Once a steady performance is reached, the media in the cell is continuously sparged with air to saturate with oxygen. The presence of excess oxygen should drastically reduce the respiration to the electrode as reported previously (Arnold 1990). As in the anaerobic case, fresh nutrients are added to the media to ensure constant activity.

Test for Establishment of Oxygen Gradient

*Shewanella oneidensis* MR-1 is used to verify the oxygen sensor principle. The strain is cultured aerobically to a fixed density on a nitrate-free formulation of media described previously (Kim 1999). This culture is used to inoculate the anode chamber. The same sterile media is saturated with oxygen and added to the media reservoir and circulated through the sample chamber. The media is formulated to contain an excess of nutrients so as not to limit metabolic activity. The media in the reservoir is sparged with sterile air to maintain oxygen saturation. The media reservoir and the cell are maintained at a constant temperature of 30° C. for this experiment. The microbes in the anode chamber are allowed to reach a steady state after being introduced in the anode chamber. The current of each individual wire is determined by measuring the voltage across drop across a resistor.

Vary Sample Oxygen Concentration

After initial testing with saturated oxygen conditions, the amount of oxygen in the media is varied to test the response of the sensor. For these tests, the media is sampled and the amount of oxygen is measured using an oxygen electrode.

Step 3: Verify Nitrate Sensor Principle (Anaerobically)

Analogous to the verification of the oxygen sensor concept, in order to validate the nitrate sensor principle, Step 3 is divided into three subtasks to confirm 1) differential MFC output with and without nitrate as an electron acceptor, 2) nitrate gradient formation and detection within the sensor, and 3) response of the sensor dependent on sample nitrate concentration.

Confirm Differential Response to Nitrate

In a conventional MFC, wild type *Shewanella oneidensis* MR-1 is conditioned in the anode chamber, utilizing anaerobic, nitrate-free media. After the culture reaches steady state performance, nitrate is added to the anode as an alternative electron acceptor and current output is monitored. Previous studies indicate that the voltage, current production output and Coulombic efficiency of the MFC will be affected by nitrate addition, with the proper carbon source and electrode potential (Sukkasem et al, 2008). In general, performance of the MFC will decrease in response to increasing anodic concentrations of nitrate, as nitrate present will provide a lower reduction potential than that available at the electrode. Using an air-cathode, addition of millimolar concentrations of nitrate to the anode medium (anaerobic) quickly reduced the output voltage of the cell and current production, especially at lower MFC internal resistance (Sukkasem et al, 2008). Since *Shewanella oneidensis* MR-1 more efficiently utilize nitrate as a terminal electron acceptor in respiration than the species used in this previous study, one would expect to observe similar losses in electrical production at lower nitrate concentrations and a more marked response in the millimolar nitrate concentration used (Cruz-Garcia et al, 2007). This result can be confirmed by poising the electrodes to +200 mV (Ag/AgCl Reference) with a potentiostat and utilizing lactate as the carbon source in the media as described (Kim 1999).

Test for Establishment of Nitrate Gradient

After the response to nitrate is established, a culture of *Shewanella oneidensis* MR-1 is grown in media as previously described (Kim 1999), with a nitrate concentration of 50 mM, to exponential phase and inoculated into the anode chamber of the nitrate sensor. Substantial variation in MFC performance has been noted at anodic nitrate concentrations below 8 mM, as such, a gradient response should be clearly visible (Sukkasem et al, 2008). Anaerobic media with the same composition is added to the media reservoir and circulated through the sample chamber. As with the oxygen sensor test cell, excess nutrients are supplied in the media and a constant temperature is maintained to ensure uniform results. Performance is judged based on current produced by the electrodes.

Vary Sample Nitrate Concentration

Once the baseline response to a high nitrate concentration is established, the nitrate sensor cell is tested with media containing a wide range of nitrate concentration. This study allows one to determine the detection threshold nitrate value using the microbial fuel cell as described herein, as well as the linearity of nitrate-response interaction. Characterization methods are the same as in baseline determination phase of the experiment, and sample nitrate concentration is confirmed using standard spectrophotometric methods (Clesceri, 1999).

Step 4: Integration of Sensor Design and Identification of Design Parameters and Challenges The final step in the initial development of a *Shewanella oneidensis* based sensor is focused on a detailed design based on the full integration of each of the components described above into a first generation sensor, and addresses additional design challenges that are not addressed in Steps 1-4. These additional issues include: oxygen diffusivity, nitrate diffusivity, metabolic and respiratory rates, dissolved oxygen rage, nitrate concentration range, and anode power density. In addition to accommodating the basic design parameters, the final design will also include features to address challenges with operational reliability and product lifespan.

Sensor Performance Modeling and Parameter Fitting

To analyze sensor performance and to prepare for future designs, the transport and reactions of the electron acceptors are modeled within the sensor. This model builds off of the analysis described above to include a two dimensional numeric analysis of the system. Experimental data about the rate of oxygen and nitrate consumption and power production under various concentrations of electron acceptors are combined with the theoretical equations for diffusive transport and diffusivity parameters. The result is a technical model capable of informing decisions about the design of sensor dimensions and validating assumptions about sensor performance.

Obtain a Mutant in Nitrate Reductase

In order to separate the contributions from oxygen and nitrate, it is necessary to utilize a strain incapable of reducing nitrate to first sense (and deplete) the oxygen without affecting the level of nitrate. A mutant strain incapable of respiration to nitrate (napA$^-$) has been previously described (Cruz-Garcia). In preparation for sensor development, the napA$^-$ strain is obtained and the phenotype and ability to transfer electrons to an electrode is verified. Verification is done in a conventional microbial fuel cell using previously described conditions and techniques (Kim 1999).

Upon construction and testing of the first generation sensor, in accordance with the methods described above, revisions to the initial design are made and additional tests are conducted for improved performance, including robustness/life-cycle testing.

EQUIVALENTS

The invention may be embodied in other specific forms without departing from the spirit or essential characteristics thereof. The foregoing embodiments are therefore to be considered in all respects illustrative rather than limiting on the invention described herein.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

What is claimed is:

1. A bio-electrochemical system for detecting the presence or absence of at least one target chemical in a medium comprising:
   a working electrode comprising a cathode or an anode; and
   at least a first electrogenic microbe disposed in proximity to the working electrode, wherein
   said electrogenic microbe interacts with the working electrode to produce an electric current which decreases in the presence of an increasing concentration of the target compound; and
   the first electrogenic microbe maintains metabolic activity in the presence of the target compound.

2. The bio-electrochemical system of claim 1, further comprising an opening by which the media medium enters the system.

3. The bio-electrochemical system of claim 1, wherein the working electrode is connected to a counter-electrode with which at least one electrogenic microbe interacts.

4. The bio-electrochemical system of claim 1, wherein the working electrode is connected to a counter-electrode with which no electrogenic microbe interacts.

5. The bio-electrochemical system of claim 1, further comprising at least one selectively permeable barrier which allows passage of the target compound to the working electrode and excludes passage of the at least first electrogenic microbe.

6. The bio-electrochemical system of claim 1, further comprising at least one selectively permeable barrier which allows passage of the target compound to the working electrode and excludes passage of any electrogenic microbe.

7. The bio-electrochemical system of claim 6, wherein the barrier is part of a membrane-electrode assembly.

8. The bio-electrochemical system of claim 6, wherein the barrier is a sterile filter.

9. The bio-electrochemical system of claim 1, wherein the at least first electrogenic microbe is a strain selected from the group consisting of *Shewanella, Psuedemonas, Geobacter, Cyanobacteria*, and mutants thereof.

10. The bio-electrochemical system of claim 9, wherein the at least first electrogenic microbe is a strain of *Shewanella oneidensis* or a mutant thereof.

11. The bio-electrochemical system of claim 1, further comprising a second electrogenic microbe, wherein the first and second electrogenic microbes are capable of detecting two or more target compounds.

12. The bio-electrochemical system of claim 1, further comprising a second electrogenic microbe.

13. The bio-electrochemical system of claim 12, comprising at least a first and a second sensor regions, separated by a selectively permeable membrane which allows passage of the target compound and excludes passage of the first and second electrogenic microbes.

14. The bio-electrochemical system of claim 13, wherein
the first sensor region comprises the working electrode, a counter-electrode, and the first electrogenic microbe disposed in proximity to the working electrode;
the second sensor region comprises an additional working electrode, an additional counter-electrode, and the second electrogenic microbe disposed in proximity to the additional working electrode; and
the first and second sensor regions are separated by the selectively permeable membrane.

15. The bio-electrochemical system of claim 1, further comprising a flow controller for modulating the volume and rate at which the medium contacts the system.

16. The bio-electrochemical system of claim 1, further comprising a consumable substrate.

17. The bio-electrochemical system of claim 1, wherein the target compound is selected from the group consisting of oxygen, nitrite ($NO_2^-$), nitrate ($NO_3^-$), fumarate, dimethyl sulfoxide, arsenate ($AsO_4^{-3}$), uranium (VI), molybdenum (VI), vanadium (V or IV), hydrogen ($H_2$), methane ($CH_4$), ammonium ($NH_4^+$), ammonia ($NH_3$), sulfide, sulfite, iron (II), arsenite, elemental sulfur)($S^0$), chromium (III), uranium (III), molybdenum (V), vanadium (IV or III), vanadate, reduced phosphate, carbohydrates, sugars, glucose, selenate, selenite, sulfate ($SO_4^-$), chromium (VI), phosphate, phosphite, iron (III), and combinations thereof.

18. The bio-electrochemical system of claim 1, wherein said system comprises a biofilm comprising a plurality of electrogenic microbes.

19. The bio-electrochemical system of claim 1, wherein target compound is in an aqueous phase or a gaseous phase.

20. The bio-electrochemical system of claim 1, further comprising at least one sensor region for detecting the target compound, wherein said region comprises a unique anode chamber and a unique cathode chamber.

21. The bio-electrochemical system of claim 20, further comprising a second sensor region for detecting a second target compound, wherein said second region comprises a unique anode chamber and a unique cathode chamber.

22. The bio-electrochemical system of claim 21, wherein said regions are separated by a selectively permeable barrier.

23. The bio-electrochemical system claim 1, further comprising a media re-circulation system.

24. A method of measuring the presence or absence of a target compound in agricultural process water comprising monitoring the water with a bio-electrochemical system comprising:
at least one working electrode comprising a cathode or an anode; and at least one first electrogenic microbe in proximity to the working electrode, wherein
said first electrogenic microbe interacts with said working electrode to produce an electrical current which decreases in the presence of an increasing concentration of the target compound; and
the first electrogenic microbe maintains metabolic activity in the presence of the target compound.

* * * * *

UNITED STATES PATENT AND TRADEMARK OFFICE
CERTIFICATE OF CORRECTION

PATENT NO. : 9,551,685 B2
APPLICATION NO. : 14/694082
DATED : January 24, 2017
INVENTOR(S) : Justin Buck et al.

It is certified that error appears in the above-identified patent and that said Letters Patent is hereby corrected as shown below:

In the References Cited, (56) Other Publications at Page 3, should read:
Line 3 Holmes, et al., "Potential Role of a Novel Psychrotolerant Member of the Family Geobacteraceae, Geopsychrobacter electrodiphilus gen. nov., sp. nov., in Electricity Production by a Marine Sediment Fuel Cell," Applied and Environmental Microbiology, Vol. 70, No. 10, pp. 6023-6030 (October 2004).

Line 36 Kim, et al., "Microbial Fuel Cell-Type Biochemical Oxygen Demand Sensor", Encyclopedia of Sensors, Vol. 6, pp. 127-138 (2006).

Signed and Sealed this
Twenty-seventh Day of March, 2018

Andrei Iancu
*Director of the United States Patent and Trademark Office*